(12) United States Patent
Lehman (10) Patent No.: US 9,308,114 B2
(45) Date of Patent: Apr. 12, 2016

(54) ADJUSTABLE NASAL PASSAGE EXPANDER

(71) Applicant: Andrew Lehman, Scottsdale, AZ (US)

(72) Inventor: Andrew Lehman, Scottsdale, AZ (US)

(*) Notice: Subject to any disclaimer, the term of this patent is extended or adjusted under 35 U.S.C. 154(b) by 95 days.

(21) Appl. No.: 14/018,004

(22) Filed: Sep. 4, 2013

(65) Prior Publication Data

US 2014/0025102 A1 Jan. 23, 2014

Related U.S. Application Data

(63) Continuation-in-part of application No. 12/927,503, filed on Nov. 16, 2010, now Pat. No. 8,561,618.

(60) Provisional application No. 61/284,604, filed on Dec. 18, 2009.

(51) Int. Cl.
*A61F 5/08* (2006.01)
*A61F 5/56* (2006.01)

(52) U.S. Cl.
CPC .... *A61F 5/08* (2013.01); *A61F 5/56* (2013.01)

(58) Field of Classification Search
CPC .... A61F 5/08; A61F 5/56; A61M 2210/0618; A61M 29/00
USPC .......... 128/848, 858, 206.23–206.25, 200.24; 606/199, 204.45
See application file for complete search history.

(56) References Cited

U.S. PATENT DOCUMENTS

| | | | | |
|---|---|---|---|---|
| 4,823,789 A * | 4/1989 | Beisang, III | ............ | 128/207.18 |
| 4,952,618 A * | 8/1990 | Olsen | .............................. | 524/17 |
| 5,284,469 A | 2/1994 | Jasen et al. | | |
| 5,669,377 A * | 9/1997 | Fenn | ......................... | 128/200.24 |
| 5,931,854 A * | 8/1999 | Dillon | ....................... | 606/204.45 |
| 5,976,173 A * | 11/1999 | Berke | ....................... | 606/204.45 |
| 6,029,658 A * | 2/2000 | De Voss | .................... | 128/200.24 |
| 6,065,470 A | 5/2000 | Van Cromvoirt et al. | | |
| 6,375,667 B1 * | 4/2002 | Ruch | .............................. | 606/199 |
| 6,470,883 B1 * | 10/2002 | Beaudry | .................. | 128/200.24 |
| 6,631,714 B2 * | 10/2003 | Von Duyke et al. | ..... | 128/200.24 |
| 6,860,263 B1 | 3/2005 | Scoggins | | |
| 7,077,140 B1 * | 7/2006 | Berke | ....................... | 128/206.25 |
| 7,456,332 B2 | 11/2008 | Beaudry | | |
| 2001/0023695 A1 | 9/2001 | Auriemma | | |
| 2005/0161046 A1 | 7/2005 | Michaels | | |
| 2008/0097517 A1 * | 4/2008 | Holmes et al. | ................ | 606/199 |
| 2008/0110469 A1 * | 5/2008 | Weinberg | ...................... | 128/863 |
| 2009/0183734 A1 | 7/2009 | Kwok | | |

OTHER PUBLICATIONS

Notice of Allowance dated Aug. 2, 2013 in U.S. Appl. No. 12/927,503.
Office Action dated Feb. 14, 2013 in U.S. Appl. No. 12/927,503.
Restriction Requirement dated Dec. 19, 2012 in U.S. Appl. No. 12/927,503.

* cited by examiner

*Primary Examiner* — Alireza Nia
*Assistant Examiner* — Kari Petrik
(74) *Attorney, Agent, or Firm* — Snell & Wilmer L.L.P.

(57) ABSTRACT

The product improves nasal passage air flow. The product may be a strip that comprises a flexible resilient material, with at least a portion of the bottom surface comprising an adhesive surface on each end. The strip may serve to dilate a user's nasal passage when the first end of the strip is secured using the first adhesive bottom surface to be proximate to an alar facial groove of the user's nose, with the second end of the strip being puled up at a slight angle and laterally to achieve desired nasal passage expansion and thereafter being secured to the user's face. The size of the strip may be larger for additional benefits and have anti-glare and/or anti-reflective features.

20 Claims, 12 Drawing Sheets

ADJUSTABLE NASAL PASSAGE EXPANDER

CROSS-REFERENCE TO RELATED APPLICATIONS

This application is a continuation-in-part of, claims priority to and the benefit of, U.S. Ser. No. 12/927,503 filed Nov. 16, 2010 entitled "ADJUSTABLE NASAL PASSAGE EXPANDER." The '503 application is the non-provisional of, claims priority to and the benefit of, provisional application U.S. Ser. No. 61/284,604 filed Dec. 18, 2009 entitled "NASAL PASSAGE EXPANDER." Both of which are incorporated herein by reference in their entirety for all purposes.

FIELD

The present disclosure is directed to articles for improving the flow of air through a person's nasal passages, and more particularly, to articles which may be applied to a person's face to assist in opening nasal passages.

BACKGROUND

Prior art nasal strips are positioned over the nose. One such strip is sold under the trademark Breathe Right. These strips claim to open the nasal passageways to reduce snoring and relieve congestion. The strip is comprised of a plastic substrate, woven material, and adhesive that is adhered by the user around the bridge of the nose. The nasal expansion occurs due to the plastic substrates memory wanting to straighten out versus being bent around the bridge of the nose. The adhesive holds the device in place which results in pulling up the nostril and achieving expansion of the air passage way.

United States Published Patent No. 2001/0023695 to Auriemma discloses a rectangular shaped nasal dilator. This dilator is applied to the Cheek area of a user away from the nose and is claimed to prevent the nasal passage of the nose from constricting during breathing. There is an adhesive layer on either end of the substrate. The strip is positioned proximate the check bone of the user with as first area of adhesive at one end of the strip. The strip extends rearwardly towards the ear of the user where the adhesive on the second end is affixed to the skin of the user between the cheek bone and the ear on the face of the user. At paragraph 0024 of the published application Auriemma states that the nasal dilator is positioned on the face beneath the eye adjacent to the nose and proximate the zygomatic bone (cheek bone). The dilator is then drawn rearwardly toward the ear whereupon the second end of the dilator is affixed to the skin so that the dilation is "affixed to the facial portion of the individual proximate the nose, beneath the eye and above the zygomatic or cheek bone and extends circumferentially rearwardly in the direction A towards the ear." The Auriemma strip is a rectangular strip with generally square adhesive areas on one side thereof. The square adhesive regions are separated by a rectangular adhesive free region. The Auriemma strips are not positioned in proximity to the outside surface of the nose. In a second embodiment there is a flexible resilient strap which extends above the head of the individual.

U.S. Pat. No. 7,456,332 to Beaudry discloses a dressing and epidermal positioning mechanism. The strips generally have a rectangular center portion and at least one circular portion with adhesive thereon. The opposite side may have a circular adhesive portion or a trapezoidal portion. The articles are positioned over the nose like the Breathe Right strips.

Kwok, U.S. Published Patent Application No. 2009/0183734 shows a strip that is positioned away from the nose and not to the nose. FIG. 2 shows a rectangular strip that has two rectangular end portions that are secured to the face along the cheekbones and which extend toward the ear and are secured to the face just in front of the ear. In an alternative, the securing device could engage behind the wearer's ear like a pair of eyeglasses. Another patent that shows a nasal dilator that is secured around the head is shown in U.S. Pat. No. 6,860,263 to Scoggins.

While there are a number of different nasal dilators, in addition to the need for other products and variations, the method and system described herein has distinct and measurable advantages in its design, function, and end results that improve air flow for users.

SUMMARY

The product includes a nasal passage expander that improves nasal airflow. The product also includes a nasal passage expander that may be worn in proximity to the side or the nose that delivers enhanced results versus the version positioned across the nose or the version that is positioned beneath the eye. The product further includes nasal passage expanders that may be worn on the cheeks on opposite sides of the nose in multiple sizes, shapes and application positions designed to achieve increased nasal airflow. The product includes a nasal passage expander that is adjustable and which gives the user the ability and flexibility to control the amount of expansion of the nasal passageways. The product also includes a nasal passage expander that extends from one edge of the nose to the side of the cheek bone that is the furthest away from the nose.

The length and positioning of the product increases the amount of nasal expansion, airflow and results for the user. The product also includes a nasal expander that increases air flow during sleep, enhances energy and impact stamina and performance during sports activities and/or delivers relief from congestion resulting from allergies, a cold or similar conditions. The product further includes a sleep, cold and/or allergy version plus a sports version. The product includes a sports version that acts as an anti-glare feature while increasing nasal airflow to enhance endurance during sport related activities. The product includes a nasal passage expander that may reduce or eliminate snoring in some users. The product also includes an adjustable nasal passage expander that does not need to be secured by straps or arms that go over the ears or around the head. The product includes a nasal passage expander that is decorative.

While there are a number of different nasal dilators available, the present disclosure incorporates unique characteristics of size, shape, positioning, methods of application, and adjustability, and furthermore achieves improved nasal airflow to satisfy the growing need for improved air flow for many users. The nasal passage expander may include a strip of a flexible sheet material, which may comprise a woven or a non-woven substrate. The expander preferably has a length greater than its width. At one end of the strip there may be a concave arcuate portion that permits the strip to be positioned as close as possible to the outer surface of the nose in the area of the side of the nose adjacent the opening of the nostril. Generally this area of the nose is called the alar facial groove or junction which is adjacent the alar sidewall. On opposite sides of the concave arc there are first and second corner members. The corner members are preferable rounded ends extending outwardly of the strip.

Extending along the length of the strip is a first sidewall and a second sidewall. The first sidewall has a generally concave configuration. However, the portion of the sidewall adjacent the corner member adjacent the first sidewall preferably has a steeper descending run than the portion of the strip that extends inwardly of the opposite end. The second sidewall is generally convex in configuration over a portion of its length. The first sidewall and the second sidewall are not parallel to each other and connect to form a curved end, the second end, i.e., the end opposite the first end with the concave arc portion discussed above. The second sidewall has an area between the first portion which is adjacent the first end of the strip with the concave arc and the center portion of the sidewall. This first portion may be provided with a slight recess. There is a second portion of the sidewall that is from the area of the center of the sidewall to the second end of the strip. The second sidewall curves upward to the second end of the strip. The arrangement of the first and second sidewalls gives the strip a configuration where the second end is higher than the first end when the strip is on a user's face.

The outside surface of the strip may be any suitable color desired. The surface may be a single color or combination of colors. In another embodiment the strip may be provided with a design, including decorative features, a logo, insignia or other figures to enhance the visual attributes of the strip. In an alternative embodiment the strip may have one end positioned on the side of the cheekbone adjacent the side of the nose and the other end of the strip on the opposite side of the cheekbone. For sports enthusiasts the outer surface of the strip may be black or a non-reflective color so that light reflecting off the cheeks does not bother the user's eyes.

The underside of the strip preferably has one or more adhesive areas. In one embodiment, the underside of the strip has a first adhesive bearing area adjacent the first end of the strip. There also is a second adhesive bearing area adjacent the second end of the strip. Between the two adhesive bearing areas there is preferably an adhesive free region. The adhesive areas on the strip can be adjusted, in terms of the type of adhesive used and the degree of its adherence to a skin surface, based on the desired use—i.e., sleep, allergy/cold relief, sports and cardio-vascular activity, etc. The shape of the adhesive surface may also be varied. The first adhesive bearing region is preferably bean shaped or shaped, i.e. having a first side that is the concave arc of the first end of the strip and an opposite side of the adhesive area having a generally convex or arcuate edge. One end of the adhesive conforms to the shape of the second end of the strip. The adhesive may be any suitable adhesive. Preferably, the adhesive utilized is a medical grade F.D.A. approved adhesive for skin contact, however other non FDA approved adhesives can be utilized as well. In certain applications an aggressive adhesive may be desirable that will not release during activities such as running, spinning, cardio, football, basketball, baseball, soccer, hockey, tennis, etc. While certain shapes have been described for the strip and the adhesive areas, it will be appreciated that there may be modifications to the shapes. The size of the strip can also vary depending on the size of the user's face and based on other variables.

The strip may be positioned with the first end, i.e., the end or edge with the concave arc adjacent to the user's nose. This area is called the alar facial groove or junction and the strip has a curved shape at one end due to the shape of the alar. The concave shape permits the strip to be secured to the face as close to the outer surface of the nose as possible. The second end is positioned along the cheek of the wearer, wrapping around the cheekbone to achieve maximum results and increased nasal airflow. To apply the strip, it is preferable that the first end be secured as close, to the outside of the nose (outer edge of the nostril) as possible. While pressure is applied to the end of the strip adjacent to the nose the strip is gently pulled out and up toward and around the cheek bone to expand the nasal passage to a desired length of nasal expansion and secure the second end on the outer end of the cheekbone is positioned on the face of the user thereby retaining the nasal passageways in a more open position, in various embodiments the end of the strip opposite the alar is secured to the area of the face on the distal side of the cheekbone with respect to the nose. While the second end of the strip can be secured to the proximate side of the cheekbone i.e., the side of the cheekbone closest to the alar groove, a longer strip may be used so that it may be secured to the distal side of the cheekbone. In various embodiments of the present invention, the strip may comprise a strip of sufficient length to at least go over/across the cheek bone to be secured thereto.

The product provides an increased air flow, so a user can breathe more freely during sleep. In addition, the strips enhance energy and impact performance during sport activities as well as deliver relief from congestion resulting from allergies or a cold or other similar conditions. Use of the strips also serves to reduce or eliminate snoring, to reduce the detrimental effects of sleep apnea, and also generally improves the rest, energy, and health of its users.

DETAILED DESCRIPTION

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and mechanical changes may be made without departing from the spirit and scope of the disclosure. Thus, the detailed description herein is presented for purposes of illustration only and not of limitation. For example, the steps recited in any of the method or process descriptions may be executed in any order and are not limited to the order presented. Moreover, any of the functions or steps may be outsourced to or performed by one or more third parties. Furthermore, any reference to singular includes plural embodiments, and any reference to more than one component may include a singular embodiment.

The adjustable nasal passage expander or nasal dilator may be a strip 5 that is made of a flexible material that is able to twist and generally conform to a contoured surface. The flexible strip material may be any suitable material, such as a thermoplastic film or sheet. The flexible strip may be a single layer, or may comprise multiple layers. The strip may also comprise a single layer throughout one portion of the strip, while comprising multiple layers throughout one or more other areas of the strip. One preferred material is polypropylene based sheet material or a Tricot sheet material. Other suitable materials include polyolefins, polyesters, etc. In various embodiments, the flexible material may also be resilient by additionally exhibiting a certain amount of elasticity. In various embodiments, the material may be flexible without any exhibiting significant elastic qualities.

The strip 5 may have a top surface 11 (FIG. 1), a bottom surface 12 (FIG. 1B), a contoured peripheral edge surface or sidewall 10 (FIG. 1A) to create a strip 5 of thickness 9. The strip 5 may have a configuration that, very broadly speaking, has a peripheral edge contour surface 10 that generally provides the strip with a very elongated triangular shape. The strip 5 may be considered to have a first end 13 and a second end 14. The first end 13 may have a concave edge portion 15 between a first convex-shaped tip 16 and a second convex-shaped tip 17, while the second end 14 may comprise a single convex-shaped tip 18. The first convex-shaped tip 16 and second convex-shaped tip 17 may each generally comprise a rounded edge surface that transitions into the elongated portion of the strip 5, as follows.

Figure 1:
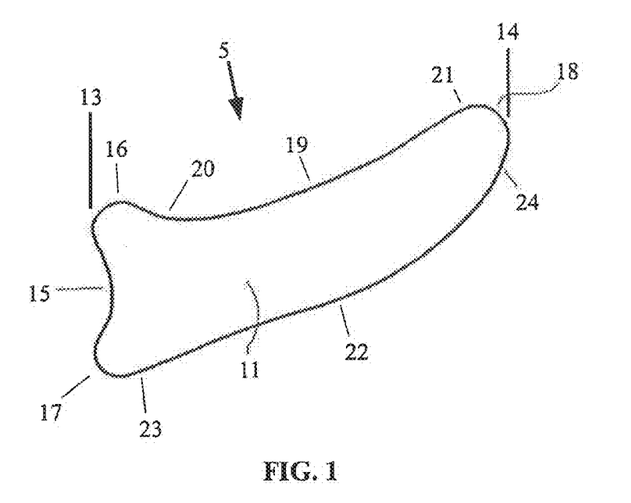
FIG. 1 is a top view of a nasal passage expander in accordance with various embodiments.
Figure 1A:
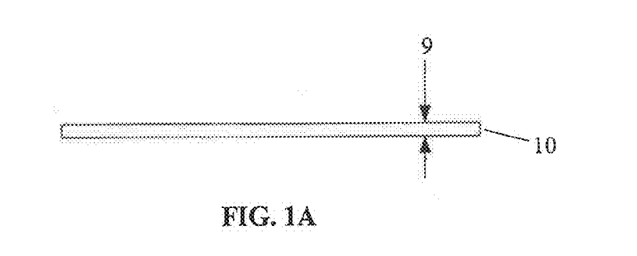
FIG. 1A is a side view of the nasal passage expander of FIG. 1, in accordance with various embodiments.

Between the first convex-shaped tip 16 at first end 13, and the convex-shaped tip 18 at second end 14, there may be a first elongated edge surface 19. The first elongated edge surface 19 may generally be formed to be concave over at least a portion of its length. A curved edge surface 20 may serve as a transition between the convex-shaped first tip 16 and the first elongated edge surface 19, and therefore, surface 20 may generally have a smaller radius of curvature than that of the second first elongated edge surface 19. Also, a curved edge surface 21 may serve as a transition between the first elongated edge surface 19 and the convex-shaped tip 18 at second end 14.

Similarly, between the second convex-shaped tip 17 at first end 13, and the convex-shaped tip 18 at second end 14, there may be a second elongated edge surface (or wall) 22. The second elongated edge surface 22 may generally be formed to be convex over at least a portion of its length. A curved edge surface 23 may serve as a transition between the convex-shaped second tip 17 and the second elongated edge surface 22. Curved transition edge surface 23 may generally be concave, and may have a varying radius of curvature to make the transition as desired. Also, a curved edge surface 24 may serve as a transition between the second elongated edge surface 22 and the convex-shaped tip 18 at second end 14.

The bottom surface 12 of the strip 5 preferably comprises two or more adhesive regions to permit temporary bonding of the strip 5 onto a persons face using pressure, as further described hereinafter, and thus may include at least one adhesive free region. The adhesive may preferably be an adhesive that is releasable, so as to permit adjustments in the placement of the strip, as described hereinafter. The strip 5 may also comprise an adhesive area in which one portion has an adhesive capability that is measurably reduced from the adhesive capability of the remaining portion, which may serve to aid in having the edges of the strip releasable for positional adjustments. However, the adhesive at the edges of the strip must nonetheless have sufficient adhesion capability so that the strip remains in place on the user's face during sleep and/or physical activity. In various embodiments, the strip 5 may preferably comprise adhesive regions 25 and 26, which are shown with cross-hatching in FIG. 1B, it may also be an adhesive which provides an amount of tack which increases with the passage of time. The adhesive may also preferably be hypoallergenic, and may include, but not be limited to, a hypoallergenic single polymer acrylate adhesive, or a hydrocolloid adhesive elastomer.

The adhesive regions of the finished strip 5 may have a removable protective strip applied thereto, in order to protect the adhesive regions prior to use. The removable protective strip should be manufactured of a suitable material or comprise a material coating adapted to resist the bonding capability of the adhesive, so that it can be peeled off of the adhesive to leave the adhesive of the strip ready for application to a user's face.

Figure 1B:
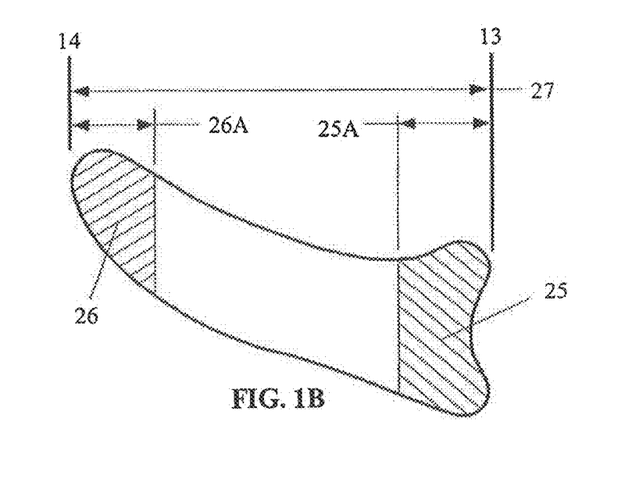
FIG. 1B is a bottom view of the nasal passage expander of FIG. 1, in accordance with various embodiments.

As seen in FIG. 1B, the first adhesive region 25 may begin at the extreme peripheral edge of the first end 13 of strip 5, and terminate along a linear edge defined by dimension 25A. The second adhesive region 26 may begin at the extreme peripheral edge of the second end 14 of strip 5, and terminate along a linear edge defined by dimension 26A. Therefore, the strip illustrated in FIG. 1B may have a total length 27, of which only the crosshatched portions denoted by dimensions 25A and 26A may have an adhesive covering, although, as previously stated, the entire length 27 of strip 5 may be covered in adhesive.

Figure 2:
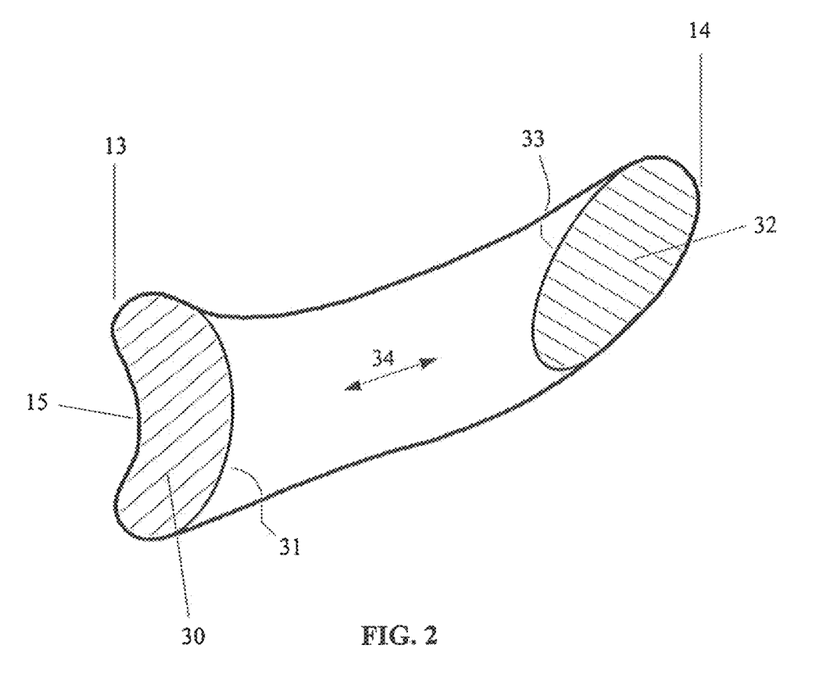
FIG. 2 is a top view of the nasal expander, in accordance with various embodiments.

Alternatively, as seen in FIG. 2, strip 5 may have a first adhesive region 30 beginning at first end 13 that can have any desired interior edge shape, being defined by an inner adhesive edge contour 31. The contour may, for example, be convex shaped to provide a certain minimum amount of adhesive centrally due to concave edge portion 15, and may thus generally resemble a "bean" shape or kidney shape. Similarly, there may be a second adhesive region 32 beginning at second end 14 that can also have any desired internal shape defined by inner adhesive edge contour 33. Thus, the second adhesive region 32 may be an ovoid or egg-shaped region.

The adhesive regions may be adapted to provide adequate retention of strip 5 on the face of a user, when applied properly, which may cause a certain amount of tension in the strip between first end 13 and second end 14, and which must be countered by the adhesive providing the requisite amount of shear strength and resistance to peeling from the user's face, until being deliberately removed therefrom. The region 34 between the first adhesive region 30 and the second adhesive region 32 may preferably be free of adhesive. Although region 34 may alternatively comprise an adhesive surface and thereby interconnect regions 30 and 32 into a single large adhesive region, maintaining region 34 free of adhesive better enables a wearer to more easily and properly apply the strip, as adhesive in region 34 could potentially contact a skin surface between the afar facial groove and the cheek area without sufficient tension existing between the first and second ends of the strip. It is this tension which serves to apply a lateral force to the alar facial groove to dilate the nasal passage. Therefore, in various embodiments of strip 5, region 34 will be free of adhesive to better enable a user to apply the strip with the requisite amount of tension to achieve the desired amount of nasal passage dilation.

Figure 4:
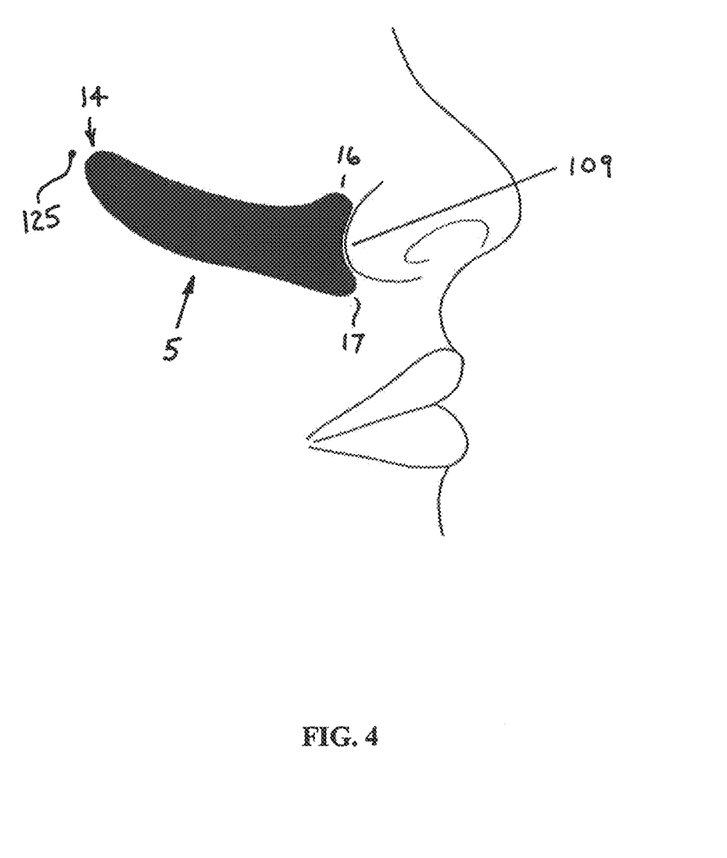
FIG. 4 shows the nasal expander in position on a user, in accordance with various embodiments.
Figure 8:
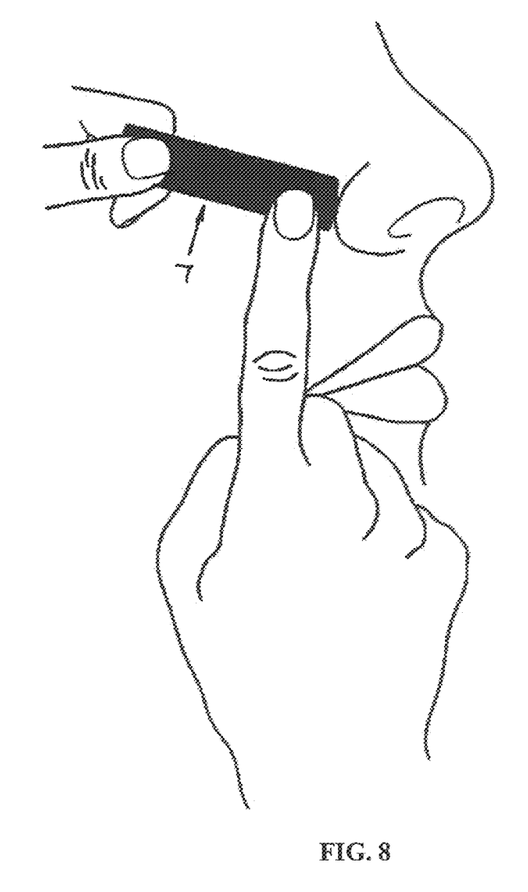
FIG. 8 shows a representative strip being applied to the alar facial groove of a user, in accordance with various embodiments.
Figure 9:
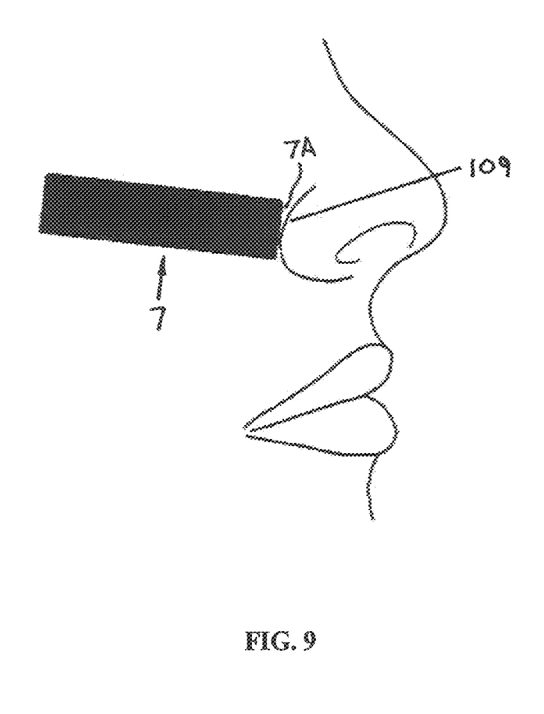
FIG. 9 shows a representative rectangular-shaped strip, in accordance with various embodiments.
Figure 10A:
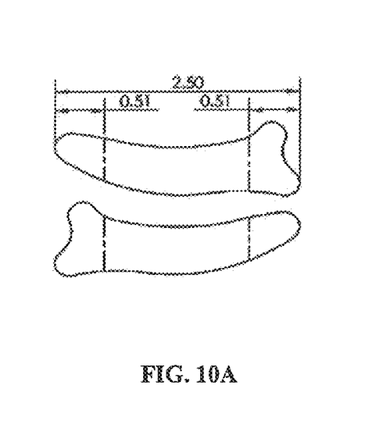
FIG. 10A shows one representative example of the size of the strip, in accordance with various embodiments.
Figure 10B:
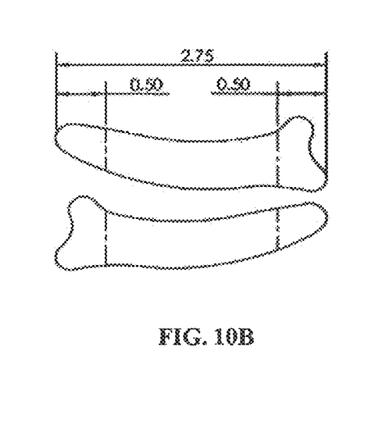
FIG. 10B shows a second representative example of the size of the strip, in accordance with various embodiments.
Figure 10C:
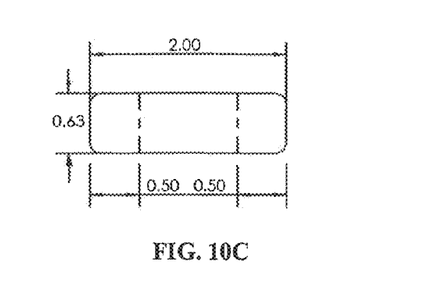
FIG. 10C show one representative example of the size of a rectangular-shaped strip, in accordance with various embodiments.
Figure 10D:
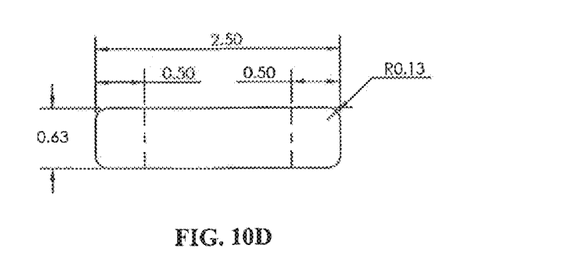
FIG. 10D show a second representative example of the size of the rectangular strip, in accordance with various embodiments.
Figure 11A:
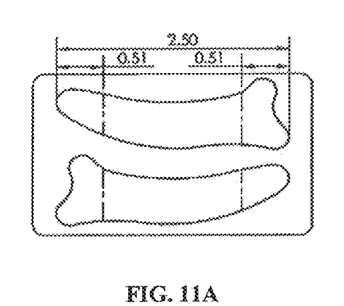
FIG. 11A shows a first sheet having a first pair of nasal passage expanders located thereon, in accordance with various embodiments.
Figure 11B:
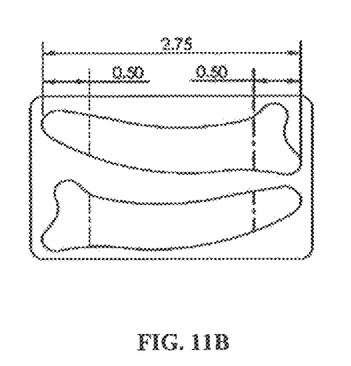
FIG. 11B shows a second sheet having a second pair of nasal passage expanders located thereon, in accordance with various embodiments.
Figure 11C:
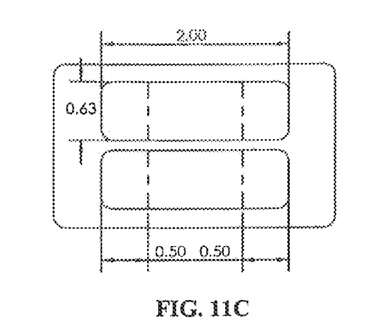
FIG. 11C show a third sheet having a first pair of rectangular-shaped nasal passage expanders located thereon, in accordance with various embodiments.
Figure 11D:
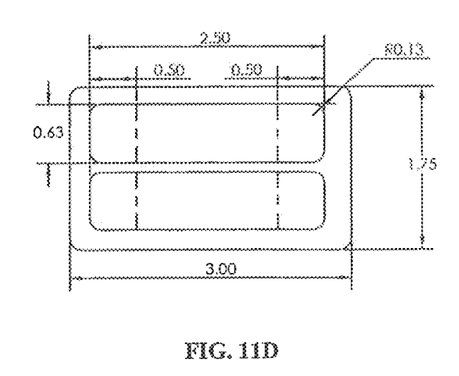
FIG. 11D shows a fourth sheet having a second pair of rectangular-shaped nasal passage expanders located thereon, in accordance with various embodiments.
Figure 12A:
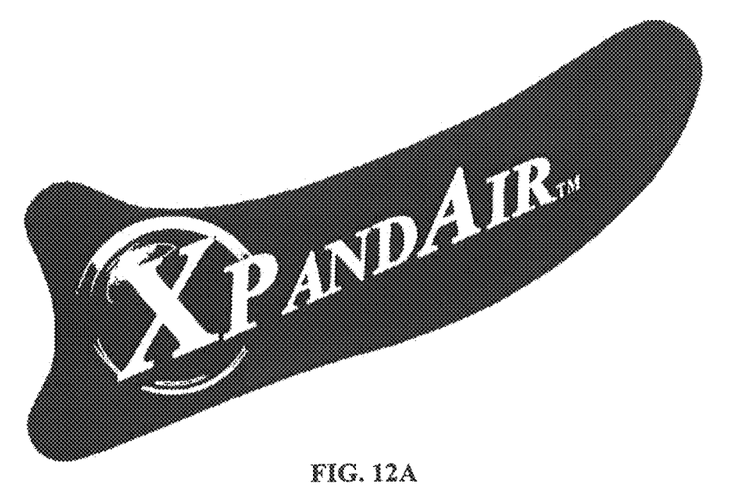
FIG. 12A is an enlarged view of the strip, exemplifying the use of graphics being displayed on the outward facing side, in accordance with various embodiments.
Figure 12B:
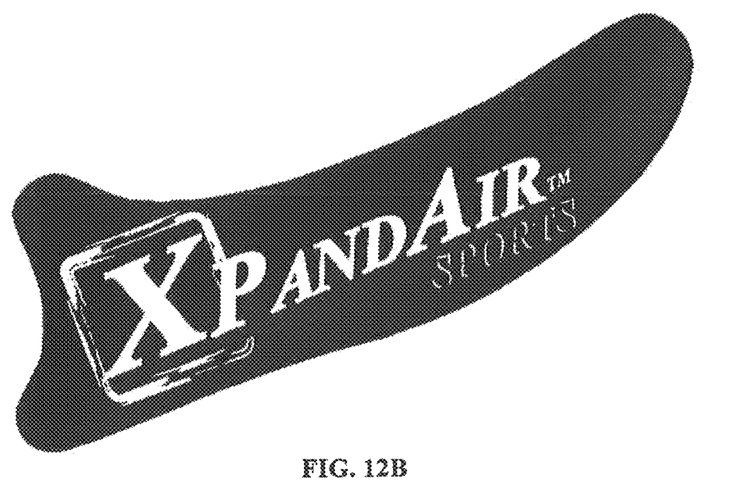
FIG. 12B is an enlarged view of the sports version of the strip, in accordance with various embodiments.

It will be appreciated that while a specific configuration for the nasal passage expander is shown in FIGS. 1 and 2 the shape of the strip and the location or shape of the adhesive regions may be tailored in a number of various way as desired, particularly as needed to suit the differently shaped and sized faces of specific users. However, one particular alternative embodiment—strip 7 is shown being applied to the alar facial groove of a user, in FIG. 8. As seen more readily in FIG. 9, the strip 7 may be rectangular-shaped, and while it may abut the alar facial groove, the flat peripheral edge surface 7A does not lend itself to closely following the nose contour of the user nearly as well as the curved peripheral edge surfaces of first end 13 of strip 5 (FIG. 4). But a black-colored strip 7, when properly positioned, nonetheless serves to dilate a user's nasal passage, although perhaps being somewhat less effective. But, the rectangular shaped strip 7 additionally serves to resemble the grease paint, shoe polish, or adhesive backed patches that athletes apply to their faces below the eye to prevent light from reflecting off from their cheeks and into the peripheral areas of the eye.

Figure 3:
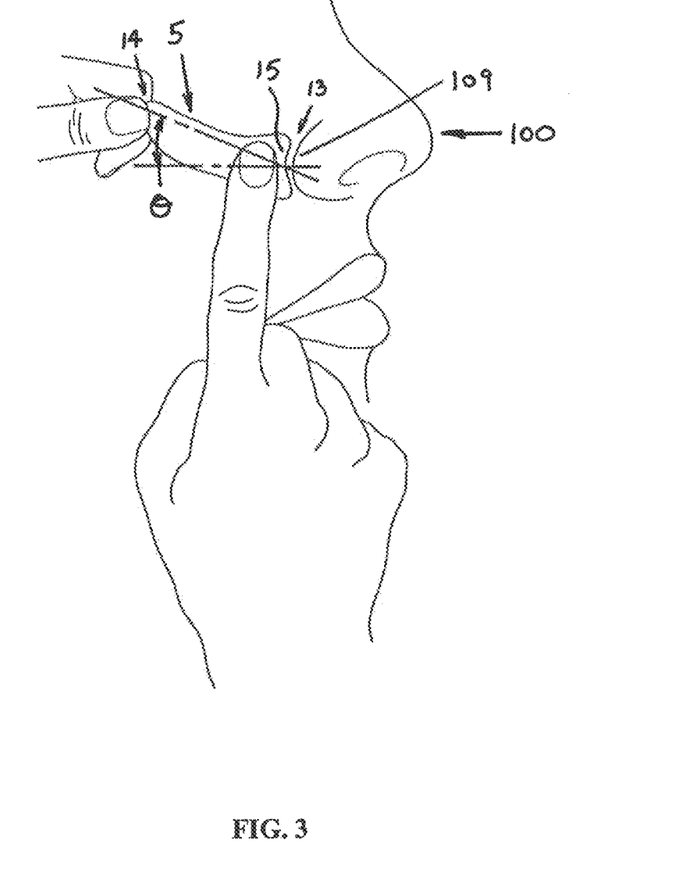
FIG. 3 is a view of the nasal passage expander being applied to a user's face, in accordance with various embodiments.
Figure 3A:
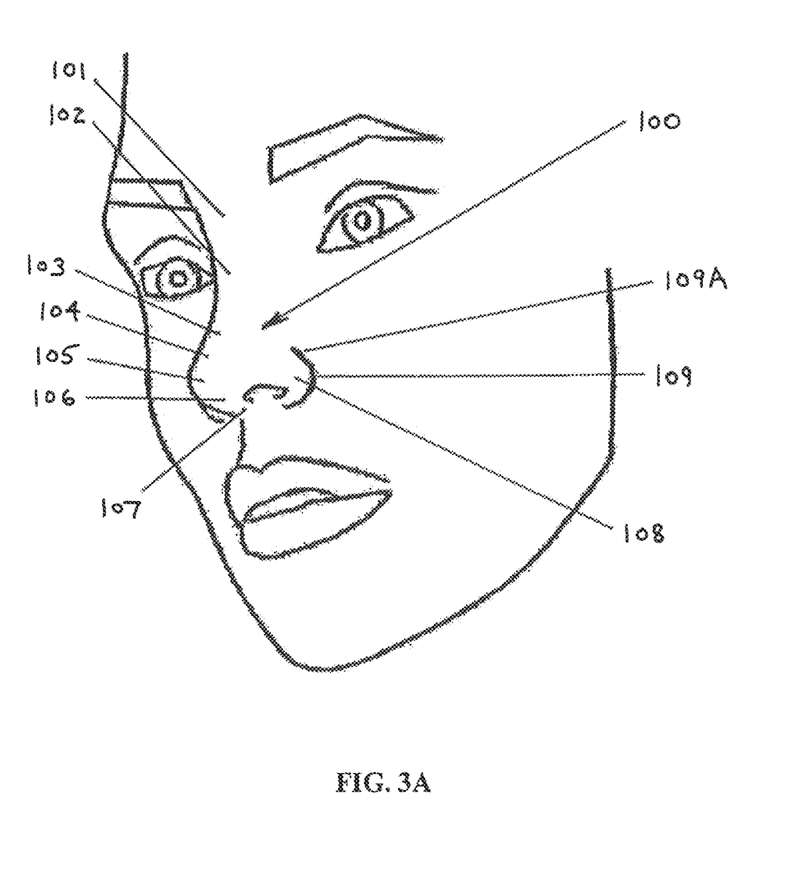
FIG. 3A is a view of a user's face, with identification thereon of anatomical features of the user's nose, in accordance with various embodiments.

The process of applying the strip 5 first requires that the protective covering be removed from at least the first adhesive region (25 or 30) at the first end 13, so that the first end 13 of the strip may first be applied to the user's face. Removal of the protective covering from the second adhesive region (26 or 32) may preferably occur later. The first adhesive region at first end 13 may preferably be applied to the portion of the user's face adjacent to the side of the nose, at the lower end of the nose, as illustrated in FIG. 3. (The surface anatomy of a person's nose is depicted and labeled in FIG. 3A to assist in understanding both the application process and the effectiveness of the strip 5 herein) This portion of the nose, at which the first end 13 is to be applied, is referred to as the alar facial groove or junction 109, which forms an edge of the alar sidewall 108.

Generally speaking, when the nasal passage expanding strip 5 is properly positioned on a user's face (FIG. 3), the strip appears to rise from the first end 13 to the second end 14 so that the second end 14 is positioned higher on the face of a user than the first end 13. To enlarge the nasal passage according to the present disclosure, the strip 5 operates to provide a lateral displacement force to the nose at the alar facial groove. However, directly lateral to the alar facial groove, on the face of many people, is the skin below the cheek bone, where the inside of the mouth lining has not quite reached the cheek bone. This portion of skin tends to be somewhat loose, and is not ideal in providing support for the lateral displacement needed for nasal passage dilation. Conversely, the skin at a person's cheekbone tends to be more firm, and is capable of better support. So, the strip 5 is adapted to angle upward slightly, through the first elongated edge surface 19 (concave) and second elongated edge surface 22 (convex), to attach at the skin proximate to the cheek bone—a little before the center of the zygomatic bone, at its center, or slightly beyond. This attachment arrangement serves to increase lateral displacement without unnecessarily distorting the person's skin and mouth, while enabling the effective nasal dilation through the following strip application process. In various embodiments of the present invention, strip 5 may comprise a strip of sufficient length to at least go over/across the cheek bone to be secured thereto. The strip may preferably be two inches or longer in length.

The shape of the first end 13 of strip 5 is crucial, because the concave edge portion 15 of strip 5 between first convex-shaped tip 16 and second convex-shaped tip 17 is deliberately contoured as shown to facilitate its placement not only in proximity to the facial groove 109 of nose 100, but to be immediately next to alar facial groove 109. The part of the triangular shape of the strip created by first convex-shaped tip 16 and second convex-shaped tip 17 serves not only to provide sufficient surface area for securing that adhesive, surface to that facial region, but also to provide a portion therein with a surface area of contact at the upper portion of the alar facial groove 109A, which is achieved by the first convex-shaped tip 16, to thereby assist in opening the nasal passage.

Although the first end 13 may be clocked at various different orientations relative to the curved portion 101 of the user's nose, the clocking should generally be such that the strip 5 extends laterally across the user's face, with the second end 14 tending to be directed slightly upward and hack towards the user's cheekbone, which generally comprises its ultimate placement, as seen in FIG. 3. This angle, .theta., may be quite small for some individuals, possibly even being zero degrees, but in general it will be between 15-30 degrees, and may preferably be, for many individuals, approximately 20 to 25 degrees, as illustrated in FIG. 3. Since the angle tends to be relatively small, the majority of the tension in the properly applied strip 5 will be resolved to be in the lateral direction and will serve to dilate the nasal passage, while any upward component of the tension force will be much smaller, and will not reduce in any way the dilation resulting from the lateral force component.

Depending on the length of the strip 5 utilized, the second end may fall just short of reaching the cheek bone before being secured to the user's face. However, in various embodiments, the strip 5 may be of sufficient length to reach and be secured to the user's face at the cheekbone of the user, or possibly may be incrementally longer to permit it to be secured at a point distal from both the nose and the cheekbone. In any case, if the first end 13 of strip 5 is not positioned correctly so as to engage the side of the nose 100, as seen in FIG. 3, final placement of the second end 14 will not be correct, which will adversely affect the nasal passage expanding capability of the strip, which will be illustrated hereinafter.

A finger may be used to apply pressure to the first end 13 of the strip 5, when it is correctly positioned, to cause the adhesive to bond to the user's skin, after which the protective covering may be removed from the second adhesive region (26 or 32). While slight pressure is applied to the first end 13 of the strip adjacent the nose, the second end 14 of strip 5 is pulled slightly upward and away from the nose to be applied to the cheek. The proper placement of the strip 5 on a user's face is shown is FIG. 4, and comprises an application in which the length of the strip 5 is such that second end 14 of the strip does not reach the cheek bone center 125, ft the user determines that the strip was improperly placed and is not providing sufficient nasal passage enlargement, or if the strip was properly oriented but an insufficient amount of pull was utilized in positioning the second end which produced an inadequate amount of dilation, the user may adjust the application by repositioning the second end 14 of the strip. The user may do so by gently releasing the second end 14, relocating it, and then refastening the adhesive surface to the user.

Figure 5:
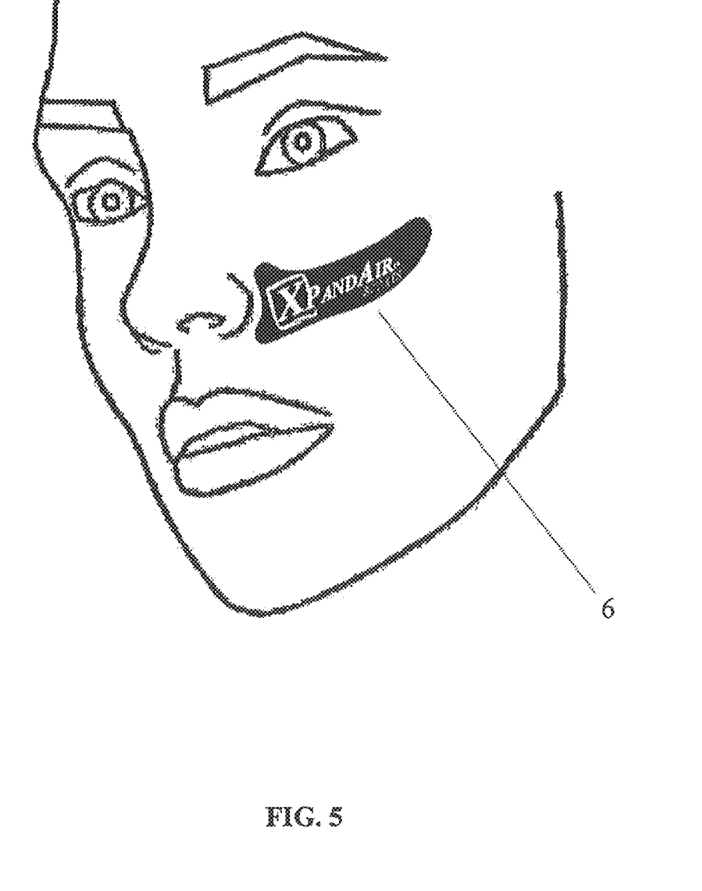
FIG. 5 is a front view of the nasal expander on a user, in accordance with various embodiments.

Although is possible to utilize only one strip upon a user's face—on either the left side or the right side—to accomplish nasal passage expansion on that particular side, it will likely be more common that a user will apply two strips—one on each side of his or her face. The left-hand and right-hand strip for both side of the face may be mirror image versions of the strip. The same steps may be followed in applying the corresponding strip 6 to the opposite side of the nose. FIG. 5 generally illustrates application of the strip on the opposite side of the nose. In addition. FIG. 5 also illustrates that a strip 6 may have a first side 11—the side without adhesive which may be visible to those looking at the user—which may be manufactured to have a tan colored material, or a clear see-through material, or to be an anti-reflective finish upon a black color for sports applications. The strip may also feature graphic art work to provide an aesthetically appealing visual appearance. The art work may be in the form of licensed images representing, for example, certain professional sports teams, or may instead be promotional art work for particular companies or products.

Figure 6:
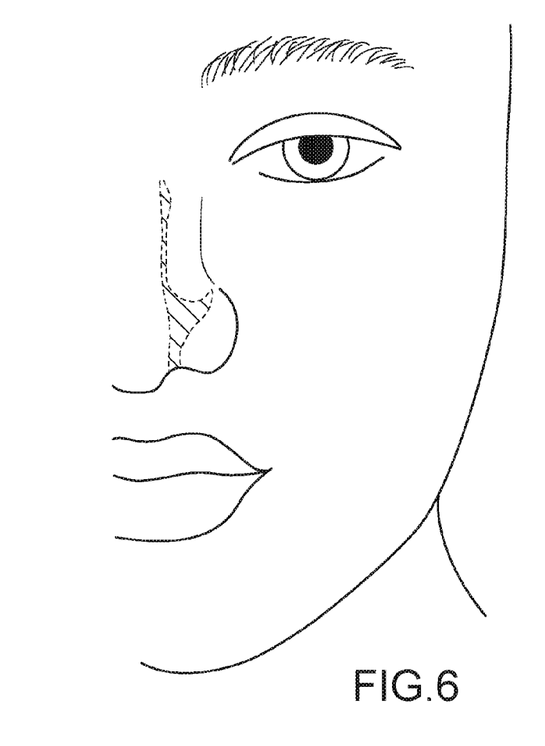
FIG. 6 shows a representation of a user's nasal passages prior to applying the expander, in accordance with various embodiments.
Figure 7:
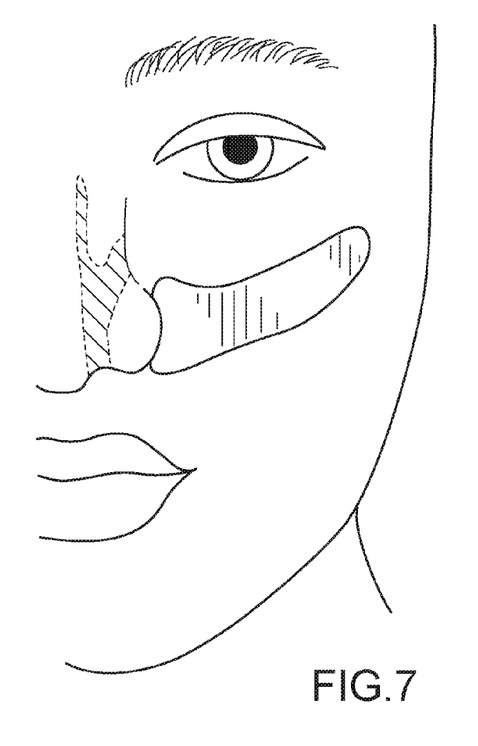
FIG. 7 shows a representation of a user's nasal passages after applying the nasal expander, in accordance with various embodiments.

FIG. 6 shows a portion of a user's face with the nasal passages shown in an untreated condition. FIG. 7 shows the expansion of the user's nasal passages, after the strip of the present application has been applied to the user's face. As call be seen from the FIGS. 6 and 7, the strip provides a means to open the nasal passageway and improve airflow. The strips provide this benefit because of the combination of the size, shape, positioning and method of application of the strip. For maximum effectiveness, the first end of the strip may preferably be adhered beyond the alar sidewall to be immediately at the alar facial groove, irregardless of the clearance shown in FIG. 5, which was shown with a gap to highlight the graphic art work. The strips 5 and 6 may be any suitable size. FIGS. 10A-10D show representative examples of different sized strips that can be used by a person who wants to take advantage of the benefits of this invention. Modifications to the size can be made depending on a number of factors including, but not limited to, the size of the user's face, the need to expand the passageways a greater distance, etc. FIGS. 11A-11D show a pair of sheets with first and second nasal expanders positioned thereon. In an alternate embodiment, the sheets may replace the protective covering, so that removal from the sheet exposes the adhesive on the strip.

Figure 13:
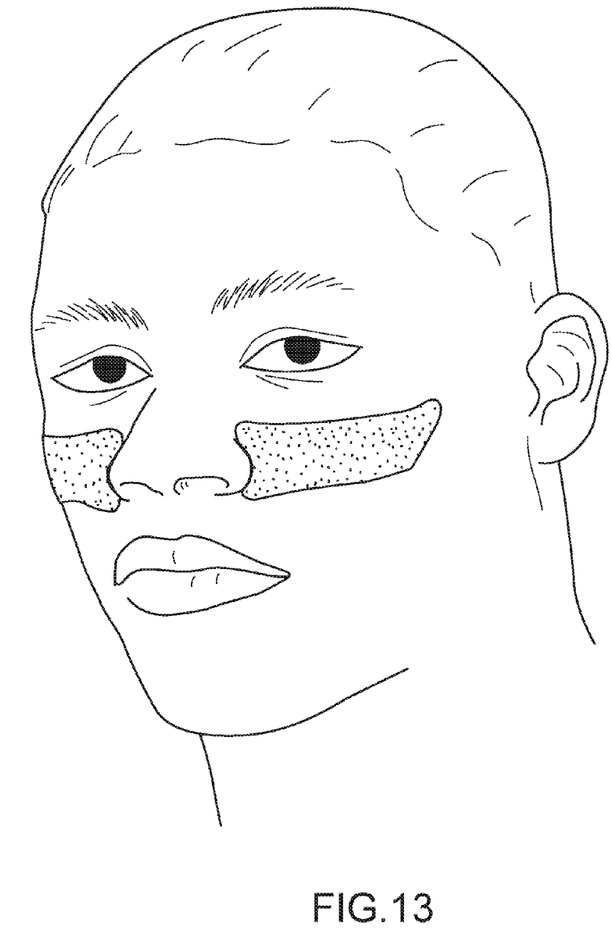
FIG. 13 is a front view of a wider nasal expander on a user affixed slightly below the orbital region of the face, in accordance with various embodiments.

In various embodiments, and as set forth in FIG. 13, certain embodiments include an increased width and/or height which allows the user to breathe better by increasing, air flow, reducing pressure and enlarging nasal passages. The increased width and/or height also gives more coverage over the face because it can be positioned higher on the face. In various embodiments, the product may be positioned just below the orbit/eye socket, depending on facial features and facial size of the user. The product may also be positioned down to where the outer nostril and cheek meet with the width being of sufficient length to be at or beyond the bend in the zygomatic arch (cheek bone) toward the ear.

While the optimal sizes were determined initially by measuring the distance from the outer nostril to the zygomatic arch for a variety of face sizes and determining the most common measurements, one skilled in the art with appreciate that the width and height of the product can be adjusted to accommodate any facial size. For example, for small to medium facial sizes, the product may be 2½" wide. For larger or extra-large facial sizes, the product may be 2⅞". The height may be ⅞" to 1" high, but the product can be produced in any height to accommodate the user. In a smaller version, the height may be ½" to 1".

The increased width and/or height of the product also enhances certain benefits due to the increased surface area of the product. The increased surface area of the product may capture more of the sun, light and other rays. The increased surface area also provides increased surface area on the bottom of the product to allow for increased, adhesive area, thereby further increasing the tack on the skin. The increased surface area also covers more of the skin on the face, thereby further protecting the skin from outside forces.

Because the upper surface of the product may include an anti-glare and/or anti-reflective material having associated benefits, the increased surface area also increases the surface area for the anti-glare and/or anti-reflective material, thereby allowing for more material. Moreover, because the product is positioned higher on the face, such positioning also provides increased anti glare and/or anti-reflective benefits because the anti-glare and/or anti-reflective material is closer to the eye.

Having the anti-glare and/or anti-reflective material incorporated into the product also minimize or eliminates the need for using other anti-glare and/or anti-reflective materials such as grease pencils and stickers (which do not provide any expansion of the nasal passages). Moreover, incorporating anti-glare and/or anti-reflective material into the top surface of the product minimizes or avoids the smearing of other anti-glare and/or anti-reflective materials like grease pencils. In various embodiments, the upper surface may include a Matte Black material which provides anti-glare and/or anti-reflective benefits.

The size, shape, placement and/or amount of adhesive (or other chemical or device for adhering the product to the face) may also be adjusted to conform to particular facial features and activities. In various embodiments, 0.700 inches of adhesive starting from an end, going inward and spread across the surface area of the bottom surface (and from top to bottom along the height) on both ends performs well. However, for certain high impact uses and/or contact sports, the shape, placement, amount, depth, width and/or height of the surface area for the adhesive may be adjusted. The adhesive may be adjusted differently around each end or around any portion of the product.

In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within, the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean one and only one unless explicitly so stated, but rather "one or more."

Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination, of the elements A, B and C may be present in a single embodiment; for example, A and B, A and C, B and C, or A and B and C.

The examples and descriptions provided merely illustrate a preferred embodiment of the present invention. Those skilled in the art and having the benefit of the present disclosure will appreciate that further embodiments may be implemented with various changes within the scope of the present invention. Other modifications, substitutions, omissions and changes may be made in the design, size, materials used or proportions, operating conditions, assembly sequence, or arrangement or positioning of elements and members of the preferred embodiment without departing from the spirit of this invention.

I claim:

1. An expander system comprising:
    a first strip and a second strip, wherein the first strip and second strip are mirror images of each other;
    wherein the first strip and the second strip are each asymmetrical about their respective central longitudinal axis;
    the first strip having:
        a flexible material;
        the flexible material having a first end, a second end, a top surface and a bottom surface;
        at least a portion of the bottom surface around the first end of the first strip comprising a first adhesive surface,
        at least a portion of the bottom surface around the second end of the first strip comprising a second adhesive surface;
        the first end of the first strip and the second end of the first strip are asymmetrical;
        the first end of the first strip and the second end of the first strip having different shapes;
        the second end of the first strip lacking a concave portion;
        wherein the first end of the first strip is configured to be secured with the first adhesive surface;
        the first end of the first strip including a concave edge portion between a first convex portion and a second convex portion to align with an alar facial groove,
        and the second end of the first strip is configured to be secured to a face of a user using the second adhesive surface;
    the second strip having:
        a flexible material;
        the flexible material having a first end, a second end, a top surface and a bottom surface;
        at least a portion of the bottom surface around the first end of the second strip comprising a first adhesive surface,
        at least a portion of the bottom surface around the second end of the second strip comprising a second adhesive surface;
        the first end of the second strip and the second end of the second strip are asymmetrical;
        the first end of the second strip and the second end of the second strip having different shapes;
        the second end of the second strip lacking a concave portion;
        wherein the first end of the second strip is configured to be secured with the first adhesive surface;
        the first end of the second strip including a concave edge portion between a first convex portion and a second convex portion to align with a second alar facial groove,
        and the second end of the second strip is configured to be secured to the face of the user using the second adhesive surface.

2. The expander system of claim 1, wherein the first end of the first strip is configured to be secured immediately adjacent to the alar facial groove of a nose of the user, wherein the first end of the second strip is configured to be secured immediately adjacent to the second alar facial groove of the nose of the user, wherein the second end of the first strip is configured to be pulled up at an upward angle and laterally, wherein the second end of the second strip is configured to be pulled up at an upward angle and laterally, and wherein the second end of the first strip is configured to be re-adjusted and re-applied on the face to re-increase the expansion of the nasal air passage.

3. The expander system of claim 1, wherein the upward angle relative to a horizontal line is between about 15 degrees and about 30 degrees.

4. The expander system of claim 1, wherein the first adhesive surface and the second adhesive surface comprises an adhesive from the group consisting of: a hypoallergenic single polymer acrylate adhesive, and a hydrocolloid adhesive elastomer.

5. The expander system of claim 1, wherein the flexible material comprises non-plastic, resilient material to maintain the expansion of the nasal air passage.

6. The expander system of claim 1, wherein the flexible material is from the group consisting of: woven material, non-woven material, polypropylene, polyolefin and polyesters.

7. The expander system of claim 1, wherein the second end of the first strip is configured to be pulled up at an upward angle and laterally, while the first end of the first strip is configured to receive temporary pressure against the face.

8. The expander system of claim 1, wherein the first adhesive surface and the second adhesive surface are configured to increase tack in response to passage of time.

9. The expander system of claim 1, wherein the first end of the first strip includes a configuration having a concave edge portion between two convex portions to align with the alar facial groove.

10. The expander system of claim 1, wherein a first edge of the first strip is concave over at least a portion of a surface of the first strip.

11. The expander system of claim 1, wherein a first edge of the first strip is concave over at least a portion of a surface of the first strip, and wherein a second edge of the first strip is convex over at least a portion of the surface of the first strip.

12. The expander system of claim 1, wherein the second end of the first strip comprises a convex-shaped tip.

13. The expander system of claim 1, wherein the second end of the first strip is configured to be secured in proximity to a cheekbone of the user.

14. The expander system of claim 1, wherein the second end of the first strip is configured to be secured to a side of a cheekbone being at least one of configured to be opposite from the nose or configured to be proximate to the alar sidewall.

15. The expander system of claim 1, wherein a top edge of the first strip is configured to be affixed adjacent and below the orbital region.

16. The expander system of claim 1, wherein a width of the first strip is between about 2.5 inches to about 3.0 inches, and wherein a height of the first strip is between about 0.5 inches to about 1.0 inch.

17. The expander system of claim 1, wherein the first adhesive surface and the second adhesive surface extend and combine to form one continuous adhesive surface.

18. The expander system of claim 1, wherein the first adhesive surface is kidney shaped.

19. The expander system of claim 1, wherein the second adhesive surface is ovoid.

20. The expander system of claim 1, wherein the top surface of the first strip comprises at least one of a non-reflective surface, an anti-glare surface or a black surface.

\* \* \* \* \*